United States Patent [19]

Shervin

[11] Patent Number: 5,304,002
[45] Date of Patent: Apr. 19, 1994

[54] METHOD OF DETERMINING BLEND TIME IN STIRRED TANKS

[75] Inventor: Carl R. Shervin, Warrington, Pa.

[73] Assignee: Rohm and Haas Company, Philadelphia, Pa.

[21] Appl. No.: 875,496

[22] Filed: Apr. 29, 1992

Related U.S. Application Data

[63] Continuation-in-part of Ser. No. 605,632, Oct. 30, 1990, abandoned.

[51] Int. Cl.⁵ .......................................... B01F 15/04
[52] U.S. Cl. ................................... 366/349; 366/127
[58] Field of Search ............. 366/348, 349, 142, 127, 366/108, 116; 68/355; 134/184; 137/88

[56] References Cited

U.S. PATENT DOCUMENTS

| | | |
|---|---|---|
| 2,540,148 | 2/1951 | Stober . |
| 3,942,767 | 3/1976 | Hanzawa ........................ 366/142 |
| 4,212,545 | 7/1980 | Lovasz ............................ 366/152 |
| 4,436,431 | 3/1984 | Strong ............................ 366/142 |
| 4,448,909 | 5/1984 | Golba et al. . |
| 4,764,019 | 8/1988 | Kaminski ........................ 366/15 |

FOREIGN PATENT DOCUMENTS 1042447 10/1958 Fed. Rep. of Germany .
255811 11/1986 Japan .

OTHER PUBLICATIONS

Effects of Stoichiometric Mixing Ratio on Epoxy Cure-A Dielectric Analysis, David R. Day, Journal of Reinforced Plastics and Composites, vol. 7, Sep. 1988, pp. 475-484.

*Primary Examiner*—Robert W. Jenkins
*Attorney, Agent, or Firm*—Thomas J. Howell

[57] ABSTRACT

Blend times of liquids are determined by measuring the rate of change in dielectric loss of stirred liquid media. The blend times for partial or complete mixing may be determined by this method, for example, mixing is essentially complete when the dielectric loss becomes constant. Tracer materials may be added to liquid mixtures to alter dielectric properties so that changes in the dielectric loss are readily measurable. This method may also be used to determine the blend times for dissolution and mixing of solid or gaseous materials with liquids.

9 Claims, 2 Drawing Sheets

METHOD OF DETERMINING BLEND TIME IN STIRRED TANKS

BACKGROUND OF THE INVENTION

This application is a continuation-in-part of co-pending application Ser. No. 605,632 filed Oct. 30, 1990, now abandoned.

This invention relates to determining blending times of organic liquids in stirred tanks by measuring dielectric loss of the liquids being mixed.

Mixing often plays a key role in the design and scaleup of industrial processes. In the case of a blending operation, mixing determines the uniformity of the final blend; choice of agitators and processing time will be critical to a successful scaleup. In the case of a chemical reaction, mixing often determines the uniformity of the product, the rate of reaction, the extent of undesired side reactions, and the molecular weight and copolymer distributions for polymerization reactions. Once a process has been defined at the laboratory or pilot scale and mixing has been determined to be important, one is then faced with the task of ensuring that comparable mixing is achieved as the process is scaled up. It is critical to be able to measure blend time on both the laboratory scale and the plant scale.

Several techniques are available for blend time measurements in the laboratory or small pilot scale. Two that are widely used are dye injection and acid-base coloration-decoloration. Both techniques work well and provide similar results for blend time. They also have the advantage of allowing the experimenter to see the mixing patterns and the location of dead zones in the vessel. They do however, have two major disadvantages: they are very subjective, relying on the observer to determine when the mixing is complete and they are restricted to clear vessels, which renders them useless for plant-scale testing in metal tanks.

A commonly used method applicable to non-transparent vessels is temperature uniformity measurement which only requires that temperature sensors be placed at various locations throughout the vessel. This method has the advantage of being simple and reliable, but there are several drawbacks. First, it requires the addition of a material that disturbs the temperature in the vessel enough that a response can be measured. Second, it requires that the rate of thermal diffusion be slower than the rate of mass diffusion or bulk mixing.

Another method that can be used in non-transparent vessels is conductivity measurement. This is accomplished by adding a small amount of a conductive salt or an acid-base mixture to generate a conductive salt. Conductivity can be monitored as the fluid mixture reaches equilibrium throughout the vessel and the mixing time can be measured as the time required to reach equilibrium or some fraction thereof. Furthermore, by knowing a priori the equilibrium conductivity, the experimenter can quantify the extent of mixing and determine whether or not dead zones exist in the vessel. This technique is rapidly becoming an accepted standard method for measuring blend time in mixing studies. Since this method requires the presence of a conductive salt, it lends itself quite readily to aqueous-phase systems.

However, the majority of industrial processes are not done in aqueous solutions and therefore require a technique applicable to organic-phase solutions.

Sichina, W., and J. Leckenby, "Dielectric Analysis Applications From Coating to Chocolate," *American Laboratory*, p. 72-80, October, 1989 and Day, D. R., "Dielectric Properties of Polymers," Micromet Instrument, Inc. Cambridge, Mass. (1987), have described the methods of measuring dielectric loss.

The two dielectric responses of a material are related to its capacitance (ability to store charge) and its conductance (ability to pass charge). These can be quantitatively expressed as the dielectric constant ($\epsilon'$) and the dielectric loss ($\epsilon''$). Dielectric responses result from a combination of several factors, including dipole interactions, ionic conduction, electrode polarization, and inhomogeneities in the material. Dielectric measurements are made over a range of frequencies, with the response dependent on the frequency. In general, high frequency measurements detect primarily the dipole interactions while the lower frequencies tend to measure the ionic conduction. When measuring dielectric properties, a span of frequencies should be used. Lower frequencies often give a stronger response, but have a longer measurement time, while higher frequencies have a short measurement time, but give a weak signal. This often requires the determination of an optimum measurement frequency.

Dielectric measurements have found many uses in the physical characterization of materials. These include the quantitative measurement of epoxy cure rates, thermal transitions, degree of crystallinity in polymers and diffusion of solvents in and out of polymers. Dielectric measurements are influenced by temperature, viscosity and chemical composition of the materials under evaluation.

SUMMARY OF THE INVENTION

This invention relates to a method of determining the blend times of liquids in a stirred vessel which comprises measuring the rate of change in dielectric loss of the liquids being mixed. One aspect of the invention involves adding a tracer to the liquids before measuring the rate of change in dielectric loss. In another aspect of the invention the liquids being mixed comprise organic liquids or organic polymers.

DETAILED DESCRIPTION OF THE INVENTION

We have now discovered that the measurement of dielectric loss effectively indicates the degree of mixing of liquids.

As used herein, liquids include liquids resulting from mixtures of one or more different liquids, dissolved or liquified solid materials and dissolved or liquified gaseous materials. In the case where a solid or gaseous material has not been completely dissolved in the final liquid solution, the term "liquid" refers to the liquid solution portion of the liquid-solid or liquid-gas mixture which contains the dissolved solid or gaseous material.

The method of determining blend time in a stirred vessel comprises:
 (a) locating one or more conductivity sensors within a vessel adapted for stirring liquids, the conductivity sensors being functionally connected to a dielectrometer;
 (b) adding liquids to be mixed to the vessel;
 (c) stirring the liquids; and
 (d) measuring the rate of change in dielectric loss as detected by the sensors while stirring to determine the degree of mixing.

In the case where the blend time for complete mixing is of interest, the rate of change in dielectric loss ($\epsilon''$) is measured until the dielectric loss becomes essentially constant, i.e., there is no further change in $\epsilon''$ over several consecutive measurements. Complete mixing refers to the uniform distribution of one liquid in another and mixing is considered essentially complete when $\epsilon''$ becomes constant. In the case where the blend time for partial mixing, i.e., degree of mixing less than 100%, is of interest, the dielectric loss value which is part of the dielectric loss/time curve that is still changing as a function of time (see FIG. 1, Example 1) indicates the relative degree of mixing. Blend time is the time required to reach a particular stage of mixing depending upon the degree of mixing which is of interest. The blend time for essentially complete mixing is usually of most interest; however, the blend time for any degree of mixing between zero and 100% may be determined by the method of the present invention.

This method also may be used to determine the blend times of liquids with solid or gaseous materials soluble in the liquids by measuring the rate of change in dielectric loss of the liquid-solid or liquid-gas mixtures being mixed. In these cases, a solid or gaseous material is added to the vessel to produce a liquid-solid or liquid-gas mixture and the rate of change in dielectric loss is measured while stirring; the order in which the liquids and solid or gaseous materials are added to the vessel is not important. The blend time for complete mixing (no further change in $\epsilon''$) corresponds to the point where the solid or gas has completely dissolved (or reached its maximum solubility point) and the dissolved material has become uniformly distributed throughout the liquid solution.

For example, the dissolution and complete mixing of a solid material is measured by adding a solvent such as mineral oil to a resin flask, followed by gradual addition of the solid material, such as ethyl cellulose, poly(ethyleneoxide), poly(vinylacetate) and the like. While stirring the solid-liquid mixture, the dielectric loss is monitored at several frequencies and the blend time for complete mixing is the point at which the rate of change in dielectric loss becomes essentially zero, i.e., $\epsilon''$ remains constant. This method is applicable to determining the blend times for complete or partial mixing of any solid material which is soluble in the liquid or liquids used.

In the case where a polymeric solid material is used, the blend time for complete mixing could be relatively long, for example several hours depending upon the amount added, and the solid material is added in stages in order not to overload the mixing capability of the agitation system being used. Measurement of the change in $\epsilon''$ in these circumstances is particularly advantageous since each addition of solid material could be made at a point where $\epsilon''$ starts to level off, thus ensuring that the amount of previously added material has mostly dissolved.

In a preferred mode of operation, the liquids to be mixed are organic liquids, preferably organic polymers. In a more preferred mode the liquids to be mixed are acrylic monomers and acrylic polymers in an organic solvent.

In another preferred mode of operation, a tracer is added to the liquids being mixed. The term "tracer" in this application refers to an organic material which alters the dielectric properties of the liquids being mixed and provides a measurable, low-noise signal for the blend time determination. Suitable tracers are toluene, xylene, heptane, dimethyl formamide (DMF), dimethyl sulfoxide and tributyl phosphate; DMF is preferred.

There are two considerations in choosing the tracer level and scanning frequency for the $\epsilon''$ measurement. First, it is important to minimize the amount of any tracer added to a solution so it does not interfere with the fluid properties. Second, the scanning frequency should be chosen to give a measurement time much shorter than the blend time. Tracer levels may vary from 0.25 to 1.0% by weight of the liquids being mixed and scanning frequency from 0.1 to 1.0 Hz (hertz); preferred conditions were 0.25% tracer and a scanning frequency of 0.5 Hz.

Workers of ordinary skill in this art will be able to select a tracer, tracer level and scanning frequency suitable for their particular system. No tracer may be required if the liquids to be mixed have sufficiently different dielectric properties.

The following examples are intended to illustrate the invention and not to limit it, except as it is limited in the claims. All ratios and percentages are by weight, and all reagents are of good commercial quality unless otherwise indicated.

EXAMPLE 1

The dielectric measurements were made using a Micromet Eumetric System II Microdielectrometer equipped with a Low Conductivity Interface. Micromet Low Conductivity Sensors purchased from Micromet Instruments, University Park, 26 Landsdown Street, Suite 150, Cambridge, Mass. 02139, were placed in the mixing vessel. The dielectrometer was interfaced with an AST 286 (IBM PC compatible) computer purchased from Evertech, 180 South Street, Murray Hill, N.J. 17974, for data acquisition using Micromet software. The mixing vessel was a one-liter resin flask coated with a platinum-iridium resistance element to provide heating and was equipped with a variable speed, variable torque stirrer. Injection point for the tracer materials and the location of the dielectric sensor were varied to test the effect of position on the mixing time curve. The agitation system was a set of three 45° pitched-blade turbines with impellers spaced approximately one-half impeller diameter apart. Acryloid® 702 poly(alkylmethacrylate) oil additive (available from Rohm and Haas Company, Philadelphia, Pa. 19105) was stirred in the flask and DMF was added after 15 minutes.

Since dielectric loss is temperature dependent, it was first necessary to establish that any signal variation caused by small temperature changes was small relative to the overall response. The relationship between $\epsilon''$ and temperature (varied from 30° to 130° C.) was measured at 1 Hz and 10 Hz. Next, it was determined whether small changes in temperature ($\pm 3°$ C.), which can be achieved on a plant scale, would affect the ability to measure $\epsilon''$. E" was found to be constant over this temperature range for a given frequency. Therefore, small temperature variations had no adverse effect on the measurements.

Careful examination of the data showed that the time at which the response began to change from the baseline was not the same for all frequencies. This was because the scans at each frequency were taken sequentially and the time of the measurement varied. For example, in a separate experiment, the scan of three frequencies measured the 0.1 Hz value at 1.87 minutes, the 1.0 Hz value at 2.02 minutes, and the 10 Hz value at 2.13 minutes. Therefore, although $\epsilon''$ began to increase for all three frequencies, a slight measurement lag occurred. The blend time for complete mixing measured by the dielectric loss method under these conditions was approximately four minutes. Similar results were obtained by visual methods for the same polymer solutions under similar mixing conditions. Dielectric measurements have the advantage of being more quantitative and reproducible than the visual methods.

Figure 1:
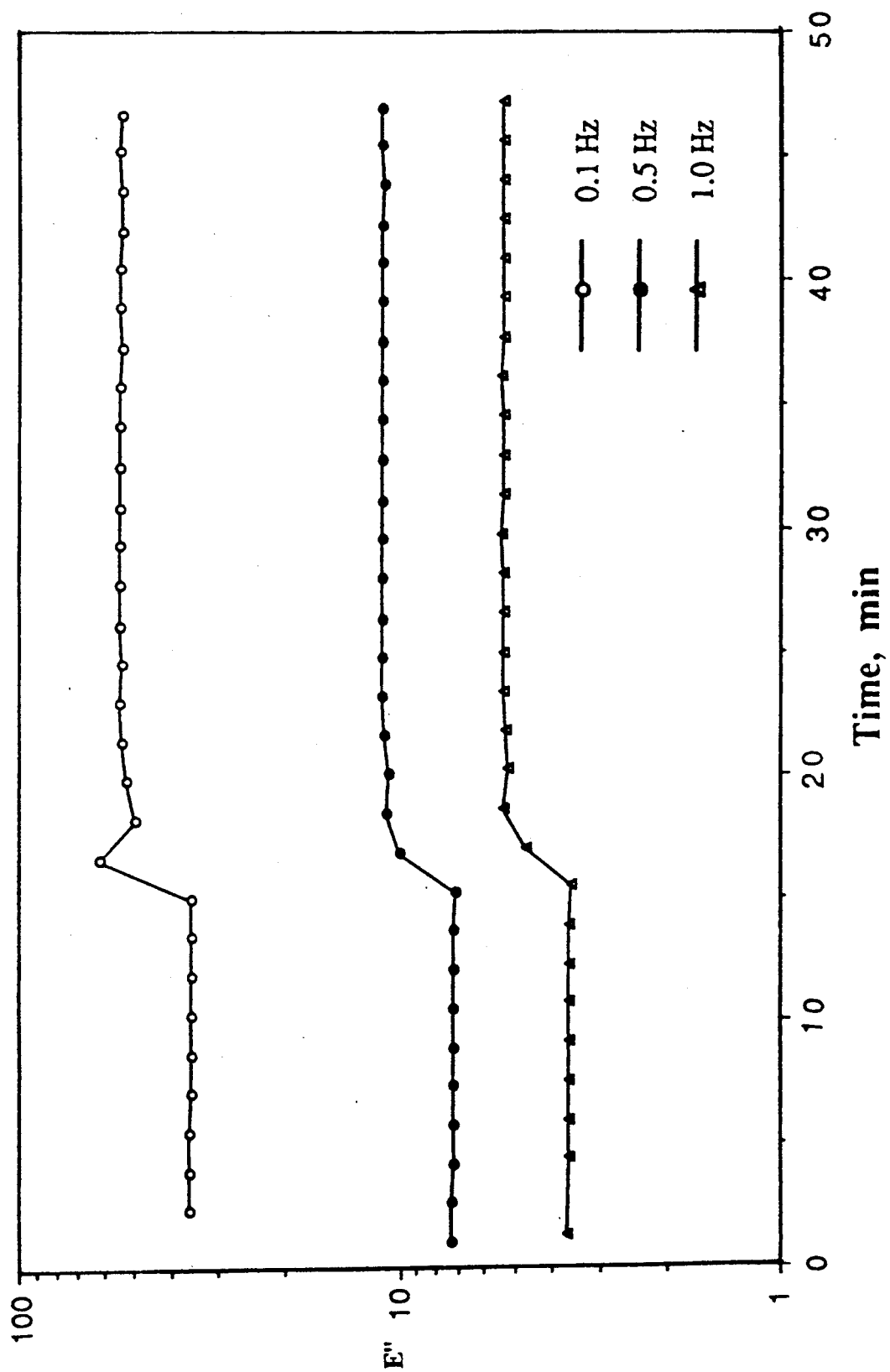
FIG. 1 shows the change in $\epsilon''$ observed for 0.25% DMF at the scanning frequencies of 0.1, 0.5 and 1.0 Hz. DMF was added after approximately 15 minutes of stirring and complete mixing was indicated when the dielectric loss became constant at 20 minutes; thus, the blend time for complete mixing in this experiment was approximately 5 minutes.
Figure 2:
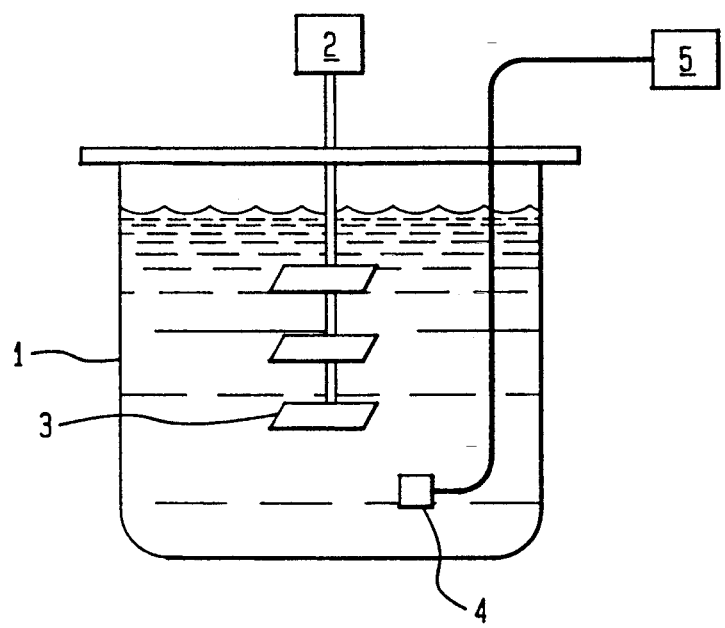

FIG. 2 is a representation of the equipment used in the process of the present invention described in Example 1. FIG. 2 shows the mixing vessel 1, the agitation system made up of a variable-speed stirrer 2 and pitched-blade turbine impellers 3, the dielectric (conductivity) sensor 4 and the dielectrometer 5 described in Example 1.

We claim:

1. A method of determining blend time of liquids comprising:
   (a) locating one or more conductivity sensors within a vessel adapted for stirring liquids, the conductivity sensors being functionally connected to a dielectrometer,
   (b) adding liquids to be mixed to the vessel,
   (c) stirring the liquids, and
   (d) measuring the rate of change in dielectric loss as detected by the sensors while stirring to determine the degree of mixing.

2. The method of claim 1 further comprising adding a tracer to the liquids after step (b) while mixing the liquids in the vessel.

3. The method claim 2 wherein the tracer comprises dimethylformamide.

4. The method of claim 2 wherein the tracer comprises dimethylformamide and the liquids to be mixed comprise organic polymers.

5. The method of claim 1 wherein the liquids to be mixed comprise organic liquids.

6. The method of claim 1 wherein the liquids to be mixed comprise organic polymers.

7. The method of claim 1 wherein the rate of change in dielectric loss is measured until the dielectric loss becomes constant to determine when mixing is essentially complete.

8. A method of determining blend time of liquids with solid or gaseous materials soluble in the liquids comprising:
   (a) locating one or more conductivity sensors within a vessel adapted for stirring liquids, the conductivity sensors being functionally connected to a dielectrometer,
   (b) adding liquids to the vessel,
   (c) stirring the liquids,
   (d) adding solid or gaseous materials to the vessel to produce the liquid-solid or liquid-gas mixture, and
   (e) measuring the rate of change in dielectric loss of the liquid-solid or liquid-gas mixture as detected by the sensors while stirring to determine the degree of mixing.

9. The method of claim 8 wherein the rate of change in dielectric loss is measured until the dielectric loss becomes constant to determine when dissolution of the solid or gaseous material and mixing are essentially complete.

* * * * *